(12) United States Patent
Wang et al.

(10) Patent No.: US 11,255,832 B2
(45) Date of Patent: Feb. 22, 2022

(54) DEVICE AND METHOD FOR DETERMINING SOLUBILITY OF ELEMENTAL SULFUR IN SULFUR-CONTAINING GAS

(71) Applicants: PETROCHINA COMPANY LIMITED, Beijing (CN); SICHUAN KELITE OIL AND GAS TECHNOLOGY CO. LTD., Chengdu (CN)

(72) Inventors: Li Wang, Beijing (CN); Zhao Ding, Beijing (CN); Fusen Xiao, Beijing (CN); Dihong Zhang, Beijing (CN); Daqing Tang, Beijing (CN); Jingyuan Chen, Beijing (CN); Ying Wan, Beijing (CN); Xuefeng Yang, Beijing (CN); Bo Kong, Beijing (CN); Tong Liu, Beijing (CN); Banghua Xie, Beijing (CN); Hua Zhou, Beijing (CN); Zhijin Pu, Beijing (CN)

(73) Assignees: PETROCHINA COMPANY LIMITED, Beijing (CN); SICHUAN KELITE OIL AND GAS TECHNOLOGY CO. LTD., Chengdu (CN)

( * ) Notice: Subject to any disclaimer, the term of this patent is extended or adjusted under 35 U.S.C. 154(b) by 265 days.

(21) Appl. No.: 16/348,603

(22) PCT Filed: May 25, 2018

(86) PCT No.: PCT/CN2018/088415
§ 371 (c)(1),
(2) Date: May 9, 2019

(87) PCT Pub. No.: WO2019/007163
PCT Pub. Date: Jan. 10, 2019

(65) Prior Publication Data
US 2020/0132647 A1    Apr. 30, 2020

(30) Foreign Application Priority Data

Jul. 6, 2017   (CN) .......................... 201710547804.7
Aug. 1, 2017   (CN) .......................... 201710645743.8

(51) Int. Cl.
*G01N 33/00*   (2006.01)
*G01N 7/04*    (2006.01)

(52) U.S. Cl.
CPC .......... *G01N 33/0036* (2013.01); *G01N 7/04* (2013.01)

(58) Field of Classification Search
CPC ........................... G01N 33/0036; G01N 7/04
See application file for complete search history.

(56) References Cited

U.S. PATENT DOCUMENTS

2007/0251296 A1   11/2007   Difoggio
2007/0264175 A1   11/2007   Iversen et al.
(Continued)

FOREIGN PATENT DOCUMENTS

CN   102053055 A   5/2011
CN   102937589 A   2/2013
(Continued)

OTHER PUBLICATIONS

Espacenet English translation of Chinese Publication CN106124354. (Year: 2016).*
(Continued)

*Primary Examiner* — Jennifer Wecker
*Assistant Examiner* — Kathryn Elizabeth Limbaugh
(74) *Attorney, Agent, or Firm* — Foley & Lardner LLP

(57) ABSTRACT

Disclosed are a device and a method for determining the solubility of elemental sulfur in a sulfur-containing gas. The device includes a displacement pump, a first sampler, a high-temperature box, a back-pressure pump, a control
(Continued)

valve, an adsorption tank, a low-temperature box, a flow meter and a collection tank. An outlet of the displacement pump is in communication with an inlet of the first sampler; an outlet of the first sampler is in communication with a first inlet of the control valve; a second inlet of the control valve is in communication with an outlet of the back-pressure pump; an outlet of the control valve is in communication with a first opening of the adsorption tank; a second opening of the adsorption tank is in communication with the flow meter; and a third opening of the adsorption tank is in communication with the collection tank.

20 Claims, 3 Drawing Sheets

(56) References Cited

U.S. PATENT DOCUMENTS

| | | | |
|---|---|---|---|
| 2012/0225009 | A1 | 9/2012 | Shen et al. |
| 2017/0191972 | A1 | 7/2017 | Sherik et al. |
| 2020/0132647 | A1 | 4/2020 | Wang et al. |

FOREIGN PATENT DOCUMENTS

| | | | |
|---|---|---|---|
| CN | 102998422 | A | 3/2013 |
| CN | 203658198 | A | 6/2014 |
| CN | 203658198 | U | 6/2014 |
| CN | 104031703 | A | 9/2014 |
| CN | 104100257 | A | 10/2014 |
| CN | 203908911 | U | 10/2014 |
| CN | 105372286 | A | 3/2016 |
| CN | 105445065 | A | 3/2016 |
| CN | 205368255 | U | 7/2016 |
| CN | 10612354 | A | 11/2016 |
| CN | 106124354 | A * | 11/2016 |
| JP | 2005-049287 | A | 2/2005 |
| WO | WO-2019/007163 | | 1/2019 |

OTHER PUBLICATIONS

English-language translation of International Search Report, PCT/CN2018/088415 (dated Sep. 18, 2018).

Third Office Action and Search Report dated Dec. 9, 2020 for Chinese 201710645743.8, along with English translation.
Fang Yue et al., Optimization and Evaluation of Calculation Models for Compression Factor of high-sulfur Natural Gas, Oil and gas field surface engineering, vol. 30 No. 7, 2011.
Zhang Yi et al., Analysis Assessment on Methods of Calculating Compression Factor of High-Sulfur Natural Gas, Inner Mongolia Petrochemical Industry, No. 9, 2010.
Zhang Yi et al., Assessment on Methods of Calculating Compression Factor of High-Sulfur Natural Gas, Journal Of Chongqing University Of Science And Technology(Natural Sciences Edition), vol. 12 No. 2, 2010.
Chinese Office Action received for application No. 20170645743.8, dated Sep. 4, 2019, 11 pages.
Chinese Office Action received for application No. 201710547804.7, dated Oct. 21, 2019, 3 pages.
Chinese Search Report received for CN application No. 201710547804.7 dated Oct. 21, 2019, 3 pages.
Chinese Search Report received for CN application No. 2017106457438 dated Aug. 27, 2019, 5 pages.
Guo Xiao et al., Sulfur deposition in sour gas reservoirs:laboratory and simulation study, Pet.Sci,Dec. 31, 2009 ,pp. 405-414.
Yang Zue-feng et al., Experimental Test and Calculation Methods of Elemental Sulfur Solubility in High Sulfure Content Gas, Natural Gas Geoscience, vol. 20, No. 3, dated Jun. 30, 2009, pp. 416-419.
Zhang Di-hong et al.; Discussion on Sampling Tecnnology of High Sulfur Gas Reservoir, Natural gas exploration and development,vol. 28,No. 1,Mar. 31, 2005,pp. 41-43, 59.
Chinese Office Action and English Translation received for application No. 201710645743.8, dated May 19, 2020, 16 pages.
Chinese Search Report and English Translation received for application No. 201710547804.7.
Chinese Search Report and English Translation received for application No. 201710645743.8, dated May 19, 2020, 6 pages.
Cui-Hualiang, Inorganic Chemistry, First Edition, Fourth Military Medical University Press. 4 Pages.
Research on Experiment and modeling of Formation Damage Caused by Sulfur Deposition of Gas Reservoirs with High H2S Content, Zhang-Wenliang, Chinese Doctoral Dissertations Full-text Database Engineering Technology Series. 11 Pages.
Shi-qikang, Elite Chemistry Basic Reader, first edition, Shanghai World Book Publishing Company. 4 Pages.
Office Action for CA App. No. 3041576 dated Jul. 8, 2020 (4 pages).

* cited by examiner

DEVICE AND METHOD FOR DETERMINING SOLUBILITY OF ELEMENTAL SULFUR IN SULFUR-CONTAINING GAS

CROSS-REFERENCE TO RELATED APPLICATIONS

This application is a National Stage Application of PCT/CN2018/088415, filed May 25, 2018, which claims the benefit of and priority to Chinese Patent Application No. 201710547804.7, filed Jul. 6, 2017, and also to Chinese Patent Application No. 201710645743.8, filed Aug. 1, 2017, all of which are incorporated herein by reference in their entireties.

TECHNICAL FIELD

The present invention relates to a device and a method for determining the solubility of elemental sulfur in a sulfur-containing gas, and belongs to the technical field of oil and gas exploration.

BACKGROUND

The dissolution and deposition of elemental sulfur is present in a high-sulfur gas reservoir compared to conventional gas reservoir development. When the pressure and temperature are lowered, the solubility of elemental sulfur in high sulfur gas will decrease. When the sulfur content in the gas is greater than the solubility of sulfur, elemental sulfur is deposited. The deposited elemental sulfur not only blocks the earth formation, greatly reduces the earth formation permeability, seriously affects the gas well productivity, but also brings harm to the normal production, transportation and management of the gas well. Therefore, it is necessary to accurately determine and calculate the solubility of elemental sulfur in high-sulfur gas reservoirs, and provide an important basis and ground for rational development, capacity allocation, scheme equation, and downstream gathering design of high-sulfur gas reservoirs.

Domestic studies on sulfur saturation (solubility of elemental sulfur in a sulfur-containing gas) are mostly based on theoretical and model studies and cannot guarantee the accuracy of the results. There are currently no experimental devices and methods for accurately determining the solubility of elemental sulfur in a sulfur-containing gas.

SUMMARY

In order to solve the above technical problems, an object of the present disclosure is to provide a device for determining the solubility of elemental sulfur in a sulfur-containing gas.

It is also an object of the present disclosure to provide a method for determining the solubility of elemental sulfur in a sulfur-containing gas.

In order to achieve the above object, in one aspect, the present disclosure provides a device for determining the solubility of elemental sulfur in a sulfur-containing gas, comprising a displacement pump, a first sampler, a high-temperature box, a back-pressure pump, a control valve, an adsorption tank, a low-temperature box, a flow meter and a collection tank, wherein an outlet of the displacement pump is in communication with an inlet of the first sampler, an outlet of the first sampler is in communication with a first inlet of the control valve, a second inlet of the control valve is in communication with an outlet of the back-pressure pump, an outlet of the control valve is in communication with a first opening of the adsorption tank, and a second opening of the adsorption tank is in communication with the flow meter; a third opening of the adsorption tank is in communication with the collection tank; the first sampler is located in the high-temperature box, the adsorption tank is located in the low-temperature box, a valve is arranged between the outlet of the first sampler and the first inlet of the control valve, and a valve is arranged between the third opening of the adsorption tank and the collection tank, and the collection tank is adapted for being heated.

In the device, preferably, the device further includes a sample dispenser, an outlet of the first sampler is in communication with an inlet of the sample dispenser, an outlet of the sample dispenser is in communication with the first inlet of the control valve, and the sample dispenser is located in the high-temperature box.

In the device, further, if the sample dispenser contains sulfur powder, the device further includes a swing device connected to the sample dispenser.

The swing device is a conventional device used in the art and its connection with the sample dispenser is also a conventional connection in the art, and the purpose of installing the swing device in the device provided by the present application is to swing the sample dispenser at a state of constant temperature and constant pressure.

In the device, preferably a filter is arranged between the outlet of the sample dispenser and the first inlet of the control valve.

In the device, preferably, the device further includes a second sampler, an inlet of the second sampler is in communication with the displacement pump, an outlet of the second sampler is in communication with the first inlet of the control valve.

In the device, preferably, a filter is arranged between the second sampler and the first inlet of the control valve.

In the device, preferably, a first coil is arranged between the outlet of the control valve and the first opening of the adsorption tank, and the first coil is located in the low-temperature box.

In the device, preferably, a second coil is arranged between the second opening of the absorption tank and the flow meter.

In the device, preferably, the flow meter includes at least two flow meters, and the at least two flow meters are connected in parallel to the downstream of the second coil, and a pneumatic valve is connected between each flow meter and the second coil.

In the device, preferably, the outlet of the flow meter is in communication with an exhaust gas treatment tank.

In the device, preferably, the device further includes a liquefaction tank, which is located in the low-temperature box, the collection tank is in communication with an inlet of the liquefaction tank, a check valve is arranged on the pipeline between the collection tank and the liquefaction tank to allow flow from the collection tank to the liquefaction tank.

In the device, preferably, the device further includes a recovery tank and a liquid injection pump, and the recovery tank and the liquid injection pump are in communication with the outlet of the liquefaction tank, respectively.

In the device, preferably, the liquid injection pump is in communication with a third opening of the adsorption tank.

In the device, preferably, the liquid injection pump is connected between the sample dispenser and the first inlet of the control valve.

The present disclosure also provides a method for determining the solubility of elemental sulfur in a sulfur-containing gas to accurately obtain the solubility of elemental sulfur in a sulfur-containing gas.

Specifically, the following technical solutions are included: collecting the sulfur-containing gas in a sulfur-containing gas reservoir, and determining a sampling temperature and a sampling pressure when the sulfur-containing gas is collected; transferring the sulfur-containing gas into a sample dispenser, allowing the sample dispenser to swing at a preset temperature and a preset pressure for a preset duration; opening a valve at an outlet end of the sample dispenser, allowing the gas in the sample dispenser to pass through a back-pressure valve and reduce the pressure to the room pressure, and then flow into the adsorption tank, wherein the adsorption tank contains a carbon disulfide liquid; passing the gas flowing out of the adsorption tank through a gas flow meter that measures the volume of the sulfur-containing gas at the room temperature and the room pressure; collecting and transferring the carbon disulfide liquid in the adsorption tank to the collection tank; heating the collection tank and cooling, and determining the mass of elemental sulfur in the collection tank; determining the room temperature and the room pressure; calculating the solubility of elemental sulfur in the sulfur-containing gas based on the sampling temperature, the sampling pressure, the room temperature, the room pressure, the mass of the elemental sulfur, and the volume of the sulfur-containing gas at the room temperature and the room pressure; wherein the outlet of the sample dispenser is in communication with the inlet of the back-pressure valve, the outlet of the back-pressure valve is in communication with the inlet of the adsorption tank, and the first outlet of the adsorption tank is in communication with the flow meter; the sample dispenser is located in the high-temperature box, the adsorption tank is located in the low-temperature box, and a valve is arranged between the outlet of the sample dispenser and the inlet of the back-pressure valve, and the collection tank is adapted for being heated.

Optionally, the calculation of the solubility of elemental sulfur in the sulfur-containing gas based on the sampling temperature, the sampling pressure, the room temperature, the room pressure, the mass of the elemental sulfur, and the volume of the sulfur-containing gas at the room temperature and the room pressure comprises: calculating the volume of the sulfur-containing gas at the standard state based on the room temperature, the room pressure, and the volume of the sulfur-containing gas at the room temperature and the room pressure; calculating the volume of the sulfur-containing gas at the sampling temperature and the sampling pressure based on the volume of the sulfur-containing gas at the standard state, the sampling temperature, and the sampling pressure; calculating the solubility of the elemental sulfur in the sulfur-containing gas based on the volume of the sulfur-containing gas at the sampling temperature and the sampling pressure and the mass of the elemental sulfur.

Optionally, the calculation equation used for the calculation of the volume of the sulfur-containing gas at the standard state based on the room temperature, the room pressure, and the volume of the sulfur-containing gas at the room temperature and the room pressure is as follows:

$$V_0 = \frac{P_1 \times V_1 \times (273.15 + T_0)}{P_0 \times (273.15 + T_1)};$$

in the equation,
$V_0$—Volume of the sulfur-containing gas at the standard state;
$P_0$—Pressure at the standard state;
$T_0$—Temperature at the standard state;
$P_1$—Room pressure
$V_1$—Volume of the sulfur-containing gas at the room temperature and the room pressure;
$T_1$—Room temperature.

Optionally, the calculation equation used for the calculation of the volume of the sulfur-containing gas at the sampling temperature and the sampling pressure based on the volume of the sulfur-containing gas at the standard state, the sampling temperature, and the sampling pressure is as follows:

$$V_1' = \frac{P_0 \times V_0 \times (273.15 + T) \times Z}{P \times (273.15 + T_0)};$$

in the equation,
$V_1'$—Volume of the sulfur-containing gas at the sampling temperature and the sampling pressure;
$P_0$—Pressure at the standard state;
$V_0$—Volume of the sulfur-containing gas at the standard state;
$T_0$—Temperature at the standard state;
P—Sampling pressure;
T—Sampling temperature;
Z—Deviation factor of the gas at the sampling temperature and the sampling pressure.

Optionally, the calculation equation used for the calculation of the solubility of elemental sulfur in the sulfur-containing gas based on the volume of the sulfur-containing gas at the sampling temperature and the sampling pressure and the mass of the elemental sulfur is as follows:

$$c = \frac{m}{V_1'};$$

in the equation,
c—Solubility of elemental sulfur in the sulfur-containing gas;
m—Mass of elemental sulfur;
$V_1'$—Volume of the sulfur-containing gas at the sampling temperature and the sampling pressure.

Optionally, prior to heating the collection tank and cooling, and determining the mass of elemental sulfur in the collection tank, the method further comprises: washing the pipeline between the sample dispenser and the adsorption tank with a carbon disulfide liquid, and collecting and transferring the carbon disulfide liquid after washing into the collection tank.

Optionally, an outlet of the gas flow meter is connected to an exhaust gas absorption tank.

Optionally, the lower end of the adsorption tank is provided with a second outlet, the second outlet of the adsorption tank is connected to the collection tank via a pipeline, and a valve is arranged on the pipeline between the adsorption tank and the collection tank.

In another aspect, the present disclosure also provides a method for determining the solubility of elemental sulfur in a sulfur-containing gas, including:
(1) collecting the sulfur-containing gas in a sulfur-containing gas reservoir, and determining a sampling temperature and a sampling pressure when the sulfur-containing gas is collected;
(2) balancing the sulfur-containing gas in the step (1) to the room pressure, and then adsorbing the sulfur-containing gas with a carbon disulfide liquid;
(3) determining the volume of the sulfur-containing gas obtained after adsorption in the step (2) at the room temperature and the room pressure;
(4) heating the carbon disulfide liquid obtained after adsorbing elemental sulfur in the step (3) to remove carbon disulfide, and weighing the obtained elemental sulfur;
(5) calculating the solubility of elemental sulfur in the sulfur-containing gas based on the sampling temperature, the sampling pressure, the room temperature, the room pressure, the mass of the elemental sulfur, and the volume of the sulfur-containing gas obtained after adsorption in the step (2) at the room temperature and the room pressure.

In the method according to the present disclosure, preferably, the step (5) of calculating the solubility of elemental sulfur in the sulfur-containing gas based on the sampling temperature, the sampling pressure, the room temperature, the room pressure, the mass of the elemental sulfur, and the volume of the sulfur-containing gas obtained after adsorption in the step (2) at the room temperature and the room pressure includes:

calculating the volume of the sulfur-containing gas at the standard state based on the room temperature, the room pressure, and the volume of the sulfur-containing gas obtained after adsorption in the step (2) at the room temperature and the room pressure;

calculating the volume of the sulfur-containing gas at the sampling temperature and the sampling pressure based on the volume of the sulfur-containing gas at the standard state, the sampling temperature, and the sampling pressure;

calculating the solubility of the elemental sulfur in the sulfur-containing gas based on the volume of the sulfur-containing gas at the sampling temperature and the sampling pressure and the mass of the elemental sulfur.

In the method, preferably, the calculation of the volume of the sulfur-containing gas at the standard state based on the room temperature, the room pressure, and the volume of the sulfur-containing gas obtained after adsorption in the step (2) at the room temperature and the room pressure comprises calculating the volume of the sulfur-containing gas at the standard state by using the following equation (1);

$$V_0 = \frac{P_1 \times V_1 \times (273.15 + T_0)}{P_0 \times (273.15 + T_1)};$$ Equation (1)

in equation (1),
$V_0$—Volume of the sulfur-containing gas at the standard state;
$P_0$—Pressure at the standard state;
$T_0$—Temperature at the standard state;
$P_1$—Room pressure
$V_1$—Volume of the sulfur-containing gas at the room temperature and the room pressure;
$T_1$—Room temperature.

In the method, preferably, the calculation of the volume of the sulfur-containing gas at the sampling temperature and the sampling pressure based on the volume of the sulfur-containing gas at the standard state, the sampling temperature, and the sampling pressure comprises calculating the volume of the sulfur-containing gas at the sampling temperature and the sampling pressure by using the following equation (2);

$$V_1' = \frac{P_0 \times V_0 \times (273.15 + T) \times Z}{P \times (273.15 + T_0)};$$ Equation (2)

in equation (2),
$V_1'$—Volume of the sulfur-containing gas at the sampling temperature and the sampling pressure;
$P_0$—Pressure at the standard state;
$V_0$—Volume of the sulfur-containing gas at the standard state;
$T_0$—Temperature at the standard state;
P—Sampling pressure;
T—Sampling temperature;
Z—Deviation factor of the gas at the sampling temperature and the sampling pressure.

In the method, preferably, the calculation of the solubility of the elemental sulfur in the sulfur-containing gas based on the volume of the sulfur-containing gas at the sampling temperature and the sampling pressure and the mass of the elemental sulfur comprises calculating the solubility of the elemental sulfur in the sulfur-containing gas by using the following equation (3);

$$c = \frac{m}{V_1'};$$ Equation (3)

in equation (3),
c—Solubility of elemental sulfur in the sulfur-containing gas;
m—Mass of elemental sulfur;
$V_1'$—Volume of the sulfur-containing gas at the sampling temperature and the sampling pressure.

In the method, preferably, the method specifically includes the following steps:
(1) collecting the sulfur-containing gas in a sulfur-containing gas reservoir, and determining a sampling temperature and a sampling pressure when the sulfur-containing gas is collected;
(2) transferring the sulfur-containing gas into a sample dispenser, and allowing the sample dispenser to swing at a preset temperature and a preset pressure for a preset duration to prevent elemental sulfur in the sulfur-containing gas from being precipitated;
(3) balancing the sulfur-containing gas in the step (2) to the room pressure, and then flowing into the adsorption tank, wherein the adsorption tank contains a carbon disulfide liquid;
(4) passing the gas flowing out of the adsorption tank through a gas flow meter, which measures the volume of the sulfur-containing gas obtained in the step (3) at the room temperature and the room pressure;
(5) collecting and transferring the carbon disulfide liquid in the adsorption tank to the collection tank; heating the collection tank to remove carbon disulfide, cooling, and determining the mass of elemental sulfur in the collection tank;
(6) calculating the solubility of elemental sulfur in the sulfur-containing gas based on the sampling temperature, the sampling pressure, the room temperature, the room pressure, the mass of the elemental sulfur, and the volume of the sulfur-containing gas obtained in the step (3) at the room temperature and the room pressure.

In the method, preferably, before the step (5), the method further includes: washing the pipeline between the sample dispenser and the adsorption tank with a carbon disulfide liquid, and collecting and transferring the carbon disulfide liquid after washing into the collection tank.

The method and device for determining the solubility of elemental sulfur in the sulfur-containing gas provided by the present disclosure can realize a balanced depressurization and smooth outflow of the gas through the control valve by displacing the sulfur-containing gas in the first sampler to the control valve through the displacement pump, and by adjusting the pressure of the back-pressure pump, thereby ensuring that the gas flow is accurately measured by the flow meter. The first sampler is located in the high-temperature box to prevent the precipitation of elemental sulfur in the gas and ensure accurate measurement results. The adsorption tank is located in the low-temperature box to ensure that the elemental sulfur in the gas is sufficiently adsorbed in the adsorption tank. The content of elemental sulfur in the gas can be obtained by heating the collection tank. Therefore, the content of elemental sulfur in the gas measured by the device and the method provided by the present disclosure is relatively accurate, and then the calculated solubility of elemental sulfur in the sulfur-containing gas based on the gas flow and the elemental sulfur content in the gas measured by the device and the method is relatively accurate.

DESCRIPTION FOR THE MAIN REFERENCE NUMBERS

Figure 1:
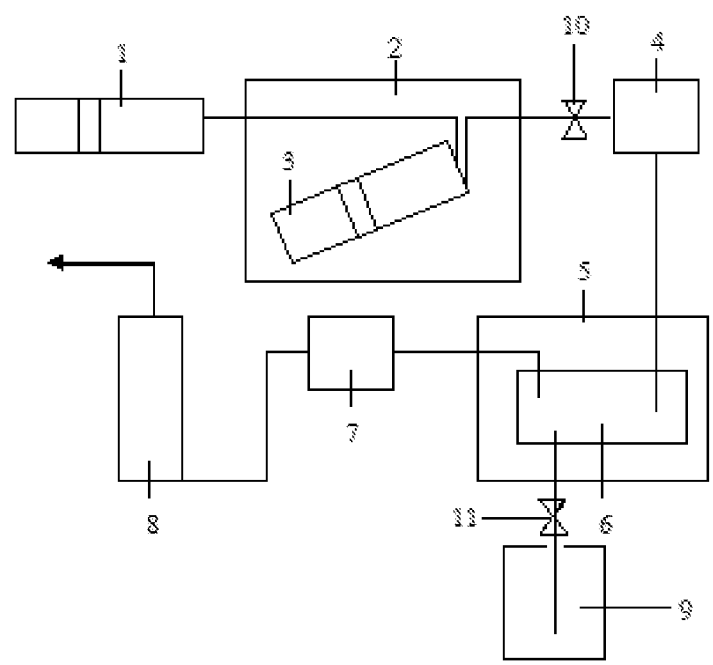
FIG. 1 is a schematic structural view of a device for determining the solubility of elemental sulfur in a sulfur-containing gas according to one embodiment.
Figure 2:
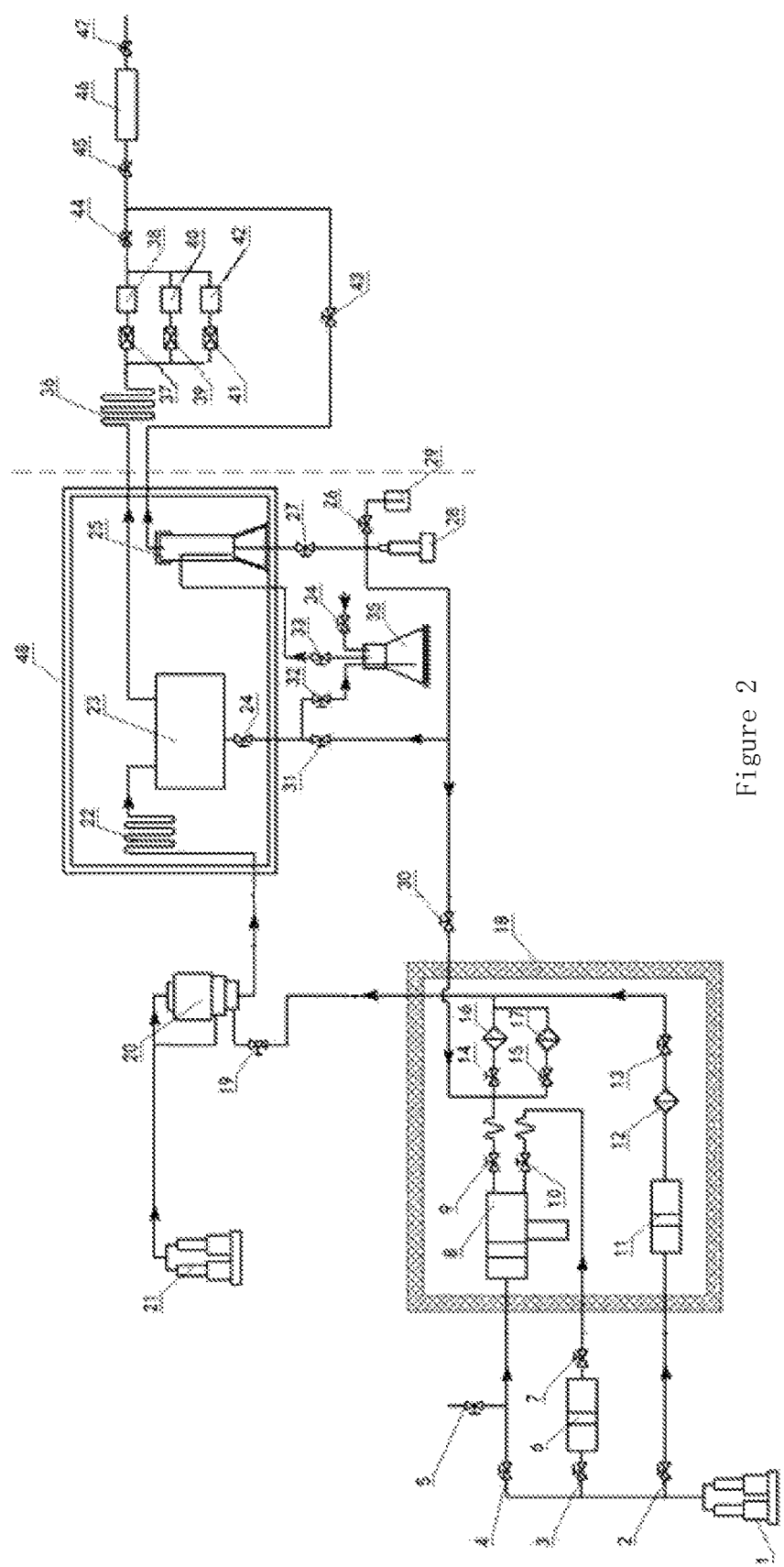
FIG. 2 is a schematic structural view of a device for determining the solubility of elemental sulfur in a sulfur-containing gas according to another embodiment.

In FIG. 1:
1. Sampling cylinder; 2. High-temperature box; 3. Sample dispenser; 4.
Back-pressure valve; 5. Low-temperature box; 6. Adsorption tank; 7. Gas flow meter; 8. Exhaust gas absorption tank; 9. Collection tank; 10. Valve; 11. Valve.
In FIG. 2:
1. Displacement pump; 2. First valve; 3. Second valve; 4. Third valve; 5.
Fourth valve; 6. First sampler; 7. Fifth valve; 8. Sample dispenser; 9. Sixth valve; 10. Seventh valve; 11. Second sampler; 12. First filter; 13. Eighth valve; 14. Ninth valve; 15. Tenth valve; 16. Second filter; 17. Third filter; 18. High-temperature box; 19. Emergency brake valve; 20. Control valve; 21. Back-pressure pump; 22. First coil; 23. Adsorption tank; 24. Eleventh valve; 25. Liquefaction tank; 26. Twelfth valve; 27. First check valve; 28. Liquid injection pump; 29. Recovery tank; 30. Second check valve; 31. Thirteenth valve; 32. Fourteenth valves; 33. Third check valve; 34. Fifteenth valve; 35. Collection tank; 36. Second coil; 37. First pneumatic valve; 38. First flow meter; 39. Second pneumatic valve; 40. Second flow meter; 41. Third pneumatic valve; 42. Third flow meter; 43. Sixteenth valve; 44. Fourth check valve; 45. Fifth check valve; 46. Exhaust gas treatment tank; 47. Sixth check valve; 48. Low-temperature box.

DETAILED DESCRIPTION

In order to better understand the technical features, objects, and advantageous effects of the present disclosure, the implementation process and the beneficial effects of the present disclosure will be described in detail below by way of specific examples and the accompanying drawings, which are intended to help the reader better understand the nature and characteristics of the present disclosure, but is not intended to limit the scope of the present disclosure.

Example 1

This example provides a device for determining the solubility of elemental sulfur in a sulfur-containing gas, which comprises a displacement pump 1, a first sampler 6, a high-temperature box 18, a back-pressure pump 21, a control valve 20, an adsorption tank 23, a low-temperature box 48, a flow meter, and a collection tank 35, wherein an outlet of the displacement pump 1 is in communication with an inlet of the first sampler 6, an outlet of the first sampler 6 is in communication with the first inlet of the control valve 20, a second inlet of the control valve 20 is in communication with the outlet of the back-pressure pump 21, the outlet of the control valve 20 is in communication with a first opening of the adsorption tank 23, a second opening of the adsorption tank 23 is in communication with the flow meter; and a third opening of the adsorption tank 23 is in communication with the collection tank 35; the first sampler 6 is located in the high-temperature box 18, the adsorption tank 23 is located in the low-temperature box 48, a fifth valve 7 is arranged between the outlet of the first sampler 6 and the first inlet of the control valve 20, and the fourteenth valve 32 is arranged between the third opening of the adsorption tank 23 and the collection tank 35, and the collection tank 35 is adapted for being heated.

In this example, the communication between adjacent devices may be realized by a pipeline, but the present disclosure is not limited thereto, it may also be achieved by direct connection or other means. In the present application, when it is described that one device is in communication with another device, it is meant that both of them can communicate by a pipeline, direct connection, or other suitable means.

When the device provided in this example is used, the gas to be measured is firstly placed in the first sampler 6, the sixth valve 9 is firstly closed, and the back-pressure pump 21 is opened to allow water in the back-pressure pump 21 to enter from the second inlet of the control valve 20. Then, the sixth valve 9 is opened to allow the gas to be measured to enter from the first inlet of the control valve 20, and then the pressure of the back-pressure pump 21 is adjusted so that the pressure difference between the pressure of the gas passing through the control valve 20 and the back pressure of the back-pressure pump 21 is in the range of 0.1 MPa, to achieve a balanced depressurization of the gas via the control valve 20, and the gas smoothly flows out of the control valve 20 and enters the adsorption tank 23. In the adsorption tank 23, the carbon disulfide liquid in the adsorption tank 23 adsorbs elemental sulfur in the sulfur-containing gas. The gas flowing out of the adsorption tank 23 enters the flow meter, and the flow meter can measure the volume of the gas. Next, the fourteenth valve 32 between the adsorption tank 23 and the collection tank 35 is opened, and the carbon disulfide liquid in the adsorption tank 23 flows into the collection tank 35, and then the collection tank 35 is heated, and carbon disulfide is volatilized as gas, and elemental sulfur remains in the collection tank 35, and the mass of the elemental sulfur is obtained by weighing. Finally, the solubility of elemental sulfur in high-sulfur gas can be calculated according to the mass of elemental sulfur, the flow of the gas, in combination with the model. In the device, the first sampler 6 is located in the high-temperature box 18 to ensure that the elemental sulfur in the gas does not precipitate; and the adsorption tank 23 is located in the low-temperature box 48, so that the carbon disulfide liquid in the adsorption tank 23 is not volatilized, and the elemental sulfur is sufficiently adsorbed in the adsorption tank 23, and therefore the device provided by the present disclosure can accurately measure the solubility of elemental sulfur in the gas.

In this example, the high-temperature box 18 may be an air bath high-temperature box or other forms of high-temperature box.

Example 2

This example provides a device for determining the solubility of elemental sulfur in a sulfur-containing gas, and a schematic structural view of the device is shown in FIG. 2. As can be seen from FIG. 2, on the basis of the device provided in Example 1, the device of this example further comprises a sample dispenser 8 and a swing device. The inlet of the first sampler 6 is in communication with the outlet of the displacement pump 1, the outlet of the first sampler 6 is in communication with the inlet of the sample dispenser 8, and the outlet of the sample dispenser 8 is in communication with the first inlet of the control valve 20, and the sample dispenser 8 is located in the high-temperature box 18 and is coupled to the swing device. A sixth valve 9 is arranged between the sample dispenser 8 and the control valve 20, and a fifth valve 7 and a seventh valve 10 are arranged between the first sampler 6 and the sample dispenser 8, and a second valve 3 is arranged between the first sampler 6 and the displacement pump 1. In this case, as shown in FIG. 2, since the volume of the high-temperature box 18 is limited, the first sampler 6 can be placed outside the high-temperature box 18, and when it is needed to measure the solubility of elemental sulfur in the gas in the first sampler 6, the gas in the first sampler 6 is displaced into the sample dispenser 8 in the high-temperature box 18. When it is needed to determine the solubility of the elemental sulfur in the saturated sulfur-containing gas, the sixth valve 9 is closed, the second valve 3, the fifth valve 7 and the seventh valve 10 are opened, and the displacement pump 1 displaces the gas in the first sampler 6 into the sample dispenser 8, and then the second valve 3, the fifth valve 7, and the seventh valve 10 are closed. An excessive amount of sulfur powder is placed in the sample dispenser 8, and the swing device is turned on to allow the sample dispenser 8 to swing in a state of constant temperature and constant pressure for 24 hours to ensure that elemental sulfur in the saturated sulfur-containing gas does not precipitate. A third valve 4 is arranged between the sample dispenser 8 and the outlet of the displacement pump 1. The third valve 4 is opened, and the displacement pump 1 drives the saturated sulfur-containing gas in the sample dispenser 8 to enter from the first inlet of the control valve 20. The pressure of the back-pressure pump 21 is adjusted so that the saturated sulfur-containing gas achieves a balanced depressurization via the control valve 20 and smoothly flows into the adsorption tank.

As shown in FIG. 2, a branch is arranged on the pipeline between the displacement pump 1 and the sample dispenser 8, and a fourth valve 5 which is used to discharge water in the sample dispenser 8 is provided on the branch.

As shown in FIG. 2, an emergency brake valve 19 may be arranged between the first inlet of the control valve 20, and the sample dispenser 8 and the first sampler 6, that is, the emergency brake valve 19 can simultaneously stop the flow from the sample dispenser 8 to the first inlet of the control valve 20. When the flow of the gas is too high and exceeds the range of the flow meter, the emergency brake valve 19 can be closed to avoid damage to the flow meter.

In this example, as shown in FIG. 2, a second filter 16 is arranged between the outlet of the sample dispenser 8 and the first inlet of the control valve 20. The second filter 16 can filter out acid, asphalt, gum, and the like from the gas flowing out of the sample dispenser 8 to avoid clogging of the pipeline. In order to make the filtering effect better, the second filter 16 and the third filter 17 can be connected in parallel and then arranged between the sample dispenser 8 and the control valve 20. A ninth valve 14 is arranged between the sample dispenser 8 and the second filter 16, and a tenth valve 15 is arranged between the sample dispenser 8 and the third filter 17. The ninth valve 14 and the tenth valve 15 are opened, and the gas in the sample dispenser 8 passes through the second filter 16 and the third filter 17, respectively, and then flows into the control valve 20.

In this example, as shown in FIG. 2, the device further includes a second sampler 11, an inlet of the second sampler 11 is in communication with the displacement pump 1, and the outlet of the second sampler 11 is in communication with the first inlet of the control valve 20. The second sampler 11 may be a downhole sampler, and the gas sample taken out from the well has a high pressure, which will achieve a balanced depressurization directly via the control valve 20. In this example, as shown in FIG. 2, a first filter 12 is arranged between the second sampler 11 and the first inlet of the control valve 20. The first filter 12 can filter out acid, asphalt, gum, and the like from the gas flowing out of the second sampler 11 to avoid clogging of the pipeline.

As shown in FIG. 2, a first valve 2 is arranged between the displacement pump 1 and the second sampler 11, and an eighth valve 13 is arranged between the second sampler 11 and the control valve 20. The first valve 2 and the eighth valve 13 are opened, and the displacement pump 1 drives the gas in the second sampler 11 to flow through the control valve 20. In this example, as shown in FIG. 2, a first coil 22 is arranged between the outlet of the control valve 20 and the inlet of the adsorption tank 23, and the first coil 22 is located in the low-temperature box 48. The gas flowing out of the control valve 20 can be cooled firstly in the first coil 22 and then enters the adsorption tank 23 to prevent the temperature of the gas entering the adsorption tank 23 from being so high to cause the carbon disulfide to volatilize.

In this example, as shown in FIG. 2, a second coil 36 is arranged between the second opening of the adsorption tank 23 and the flow meter. The gas velocity of the gas flowing out of the adsorption tank 23 can be firstly reduced through the second coil 36, thereby avoiding the gas flow rate being so high to exceed the flow meter's range.

In this example, as shown in FIG. 2, there are three flow meters. The three flow meters are connected in parallel and then arranged after the second coil 36, a pneumatic valve is connected between each flow meter and the second coil 36.

As shown in FIG. 2, the first flow meter 38 is in series with the first pneumatic valve 37, the second flow meter 40 is in series with the second pneumatic valve 39, and the third flow meter 42 is in series with the third pneumatic valve 41. The three flow meters have different ranges, a flow meter of an appropriate range can be selected according to the requirement, to ensure a more accurate measurement of gas flow. The gas is introduced into the designated flow meter by controlling the first pneumatic valve 37, the second pneumatic valve 39, and the third pneumatic valve 41. This example is described with three flow meters, but the present disclosure is not limited thereto.

In this example, as shown in FIG. 2, the outlet of the flow meter is in communication with the exhaust gas treatment tank 46. A fourth check valve 44 is arranged between the exhaust gas treatment tank 46 and the flow meter. When the gas flows out of the outlet of the flow meter, the fourth check valve 44 is opened, so that the gas can enter the exhaust gas treatment tank 46 to prevent contamination of the environment. A sixth check valve 47 is arranged on the outlet pipeline of the exhaust gas treatment tank 46. The sixth check valve 47 is opened, and the gas treated by the exhaust gas treatment tank 46 can flow into other devices.

In this example, as shown in FIG. 2, the device further comprises a liquefaction tank 25 located in the low-temperature box 48, the collection tank 35 is in communication with an inlet of the liquefaction tank 25, and a check valve 33 is arranged on the pipeline between the collection tank 35 and the liquefaction tank 25 to allow flow from the collection tank 35 to the liquefaction tank 25. A fifteenth valve 34 is arranged on the pipeline communicating with the collection tank 35. When the collection tank 35 is heated, the fifteenth valve 34 is opened and an inert gas which is dry and does not react with elemental sulfur and carbon disulfide, such as nitrogen, is injected, and the inert gas carries all of the carbon disulfide gas in the collection tank 35 out of the collection tank 35 and enters the liquefaction tank 25. The carbon disulfide gas entering the liquefaction tank 25 is liquefied and deposited to the lower portion of the liquefaction tank 25. A sixteenth valve 43 is arranged between the outlet of the upper end of the liquefaction tank 25 and the exhaust gas treatment tank 46, and the sixteenth valve 43 is opened, and the inert gas is discharged from the upper end of the liquefaction tank 25 and enters the exhaust gas treatment tank 46. The outlet of the upper end of the liquefaction tank 25 is connected to the fifth check valve 45 through a pipeline. At this time, a fourth check valve 44 is required between the fifth check valve 45 and the flow meter, and when the sixteenth valve 43 is opened, the fourth check valve 44 is closed to prevent the inert gas from flowing back into the flow meter.

In this example, as shown in FIG. 2, the device further includes a recovery tank 29 and a liquid injection pump 28, and the recovery tank 29 and the liquid injection pump 28 are in communication with the outlet of the liquefaction tank 25, respectively. A first check valve 27 is arranged on a pipeline leading from the liquefaction tank 25 to the recovery tank 29 and the liquid injection pump 28, and the first check valve 27 is opened, and the carbon disulfide liquid in the liquefaction tank 25 flows to the liquid injection pump 28 and the recovery tank 29. A twelfth valve 26 may be arranged between the first check valve 27 and the recovery tank 29. When it is needed to inject carbon disulfide into the adsorption tank, the twelfth valve 26 can be closed, so that the carbon disulfide liquid in the liquefaction tank 25 flows into the liquid injection pump 28.

In this example, as shown in FIG. 2, the liquid injection pump 28 is in communication with the third opening of the adsorption tank 23. A thirteenth valve 31 may be arranged between the liquid injection pump 28 and the third opening of the adsorption tank 23, and when it is needed to inject carbon disulfide into the adsorption tank 23, the thirteenth valve 31 is opened, and the liquid injection pump 28 injects carbon disulfide into the liquefaction tank 25.

As shown in FIG. 2, an eleventh valve 24 may be arranged on the pipeline leading from the liquid injection pump 28 to the fourteenth valve 32 and the thirteenth valve 31. The eleventh valve 24 can serve as a master control valve. Only when the eleventh valve 24 is opened, the carbon disulfide liquid can flow into the collection tank 35 through the fourteenth valve 32, or can flow into the adsorption tank 23 through the thirteenth valve 31 from the liquid injection pump 28.

In this example, as shown in FIG. 2, the liquid injection pump 28 may be connected between the sample dispenser 8 and the first inlet of the control valve 20. A second check valve 30 may be arranged on the pipeline between the first sampler 6 and the first inlet of the control valve 20 from the liquid injection pump 28, so that when the second check valve 30, the ninth valve 14 and the tenth valve 15 are opened, the carbon disulfide liquid in the liquid injection pump 28 flows through the second filter 16 and the third filter 17, and cleans impurities or elemental sulfur remaining in the pipeline to prevent clogging of the pipeline.

In FIGS. 1 and 2, the arrows represent the direction of flow of gas or liquid in the pipeline.

Example 3

This example provides a method for determining the solubility of elemental sulfur in a sulfur-containing gas, which is implemented on the basis of an experimental device as shown in FIG. 1, including a high-temperature box 2, a sample dispenser 3, a back-pressure valve 4, a low-temperature box 5, an adsorption tank 6, a flow meter 7 and a collection tank 9; wherein the outlet of the sample dispenser 3 is in communication with an inlet of the back-pressure valve 4, an outlet of the back-pressure valve 4 is in communication with an inlet of the adsorption tank 6, and a first outlet of the adsorption tank 6 is in communication with the flow meter 7; the sample dispenser 3 is located in the high-temperature box 2, the adsorption tank 6 is located in the low-temperature box 5, and a valve 10 is arranged between the outlet of the sample dispenser 2 and the inlet of the back-pressure valve 3, and the collection tank 9 is adapted for being heated.

Figure 3:
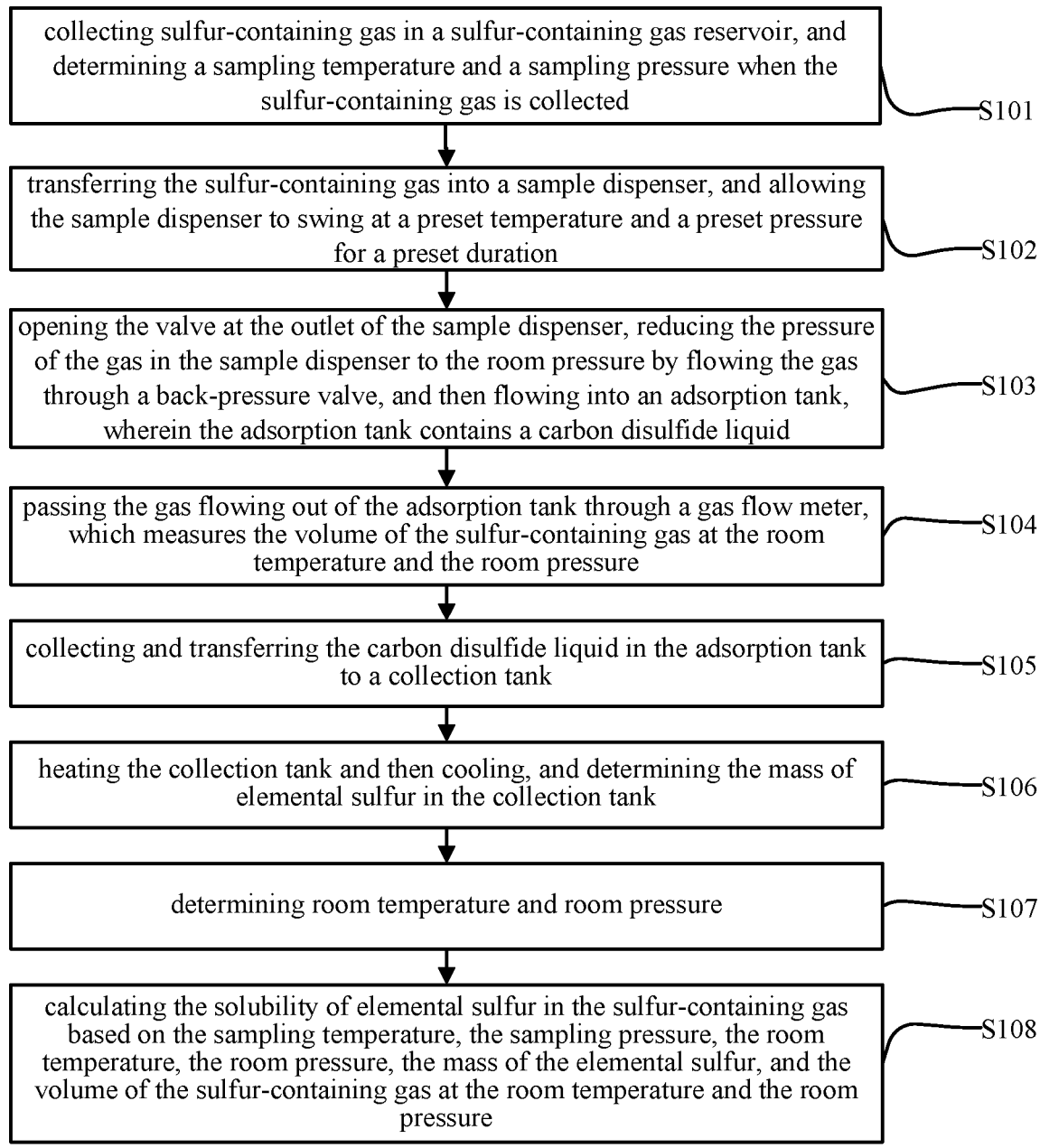
FIG. 3 is a process flow chart of a method for determining the solubility of elemental sulfur in a sulfur-containing gas according to an example embodiment.

The method for determining the solubility of elemental sulfur in the sulfur-containing gas is shown in FIG. 3, and comprises steps S101 to S108. Each step will be specifically described below.

S101: Collecting the sulfur-containing gas in a sulfur-containing gas reservoir, and determining a sampling temperature and a sampling pressure when the sulfur-containing gas is collected.

As shown in FIG. 1, the experimental device further comprises a sampling cylinder 1, and an outlet of the sampling cylinder 1 is connected to an inlet of the sample dispenser. The sampling cylinder 1 can be used to collect the sulfur-containing gas in the sulfur-containing gas reservoir, and the sampling pressure and the sampling temperature when the sulfur-containing gas is collected are measured by a pressure gauge and a thermometer.

S102: Transferring the sulfur-containing gas into the sample dispenser, allowing the sample dispenser to swing at a preset temperature and a preset pressure for a preset duration.

After the sample of sulfur-containing gas is collected from the gas reservoir, a part of the elemental sulfur dissolved in the sulfur-containing gas may be precipitated due to changes in temperature and pressure. In order to ensure the accuracy of the experiment, the sulfur-containing gas is firstly transferred into the sample dispenser located in the high-temperature box, and swayed for the preset duration to prevent elemental sulfur from being precipitated. The preset temperature, the preset pressure and the preset duration may be set according to actual conditions. For example, the preset temperature may be 80° C., the preset pressure may be 1 MPa, and the preset duration may be 24 hours.

S103: Opening the valve at the outlet of the sample dispenser, reducing the pressure of the gas in the sample dispenser to the room pressure by flowing the gas through a back-pressure valve, and then flowing into an adsorption tank, wherein the adsorption tank contains a carbon disulfide liquid.

In order to prevent the case in which the pressure of the gas flowing out of the sample dispenser is too high, resulting in an excessive flow rate of the gas, which in turn causes insufficient adsorption of sulfur in the gas in the carbon disulfide liquid, the gas firstly achieves a balanced depressurization through the back-pressure valve 4, and then smoothly flows out of the back-pressure valve 4 and enters the adsorption tank 6.

S104: Passing the gas flowing out of the adsorption tank through a gas flow meter that measures the volume of the sulfur-containing gas at the room temperature and the room pressure.

Herein, in order to ensure the accuracy of the gas volume measurement, a gas flow meter of a suitable range should be selected.

In this example, the room temperature and the room pressure refer to the temperature and the pressure of the laboratory in which the experimental device is located when the experiment is conducted.

S105: Collecting and transferring the carbon disulfide liquid in the adsorption tank to the collection tank.

In order to facilitate the transfer of carbon disulfide in the adsorption tank to the collection tank, as shown in FIG. 1, the lower end of the adsorption tank 6 may be provided with a second outlet, and the second outlet of the adsorption tank 6 is connected to the collection tank 9 through a pipeline, and a valve 11 is arranged on the pipeline between the adsorption tank 6 and the collection tank 9.

After the sulfur-containing gas is adsorbed in the adsorption tank 6, the valve 11 is opened, and the carbon disulfide liquid in the adsorption tank 6 flows into the collection tank 9 via the pipeline, which is convenient to operate.

S106: Heating the collection tank and cooling, and determining the mass of elemental sulfur in the collection tank.

When the collection tank is heated, the carbon disulfide liquid in the collection tank is converted into a gas and volatilized, and the elemental sulfur remains in the collection tank. After the collection tank is cooled, the mass of elemental sulfur in the collection tank is determined, that is, the mass of elemental sulfur dissolved in the sulfur-containing gas.

S107: Determining the room temperature and the room pressure.

The pressure of the gas measured by the flow meter is the pressure at the room temperature and the room pressure. For the convenience of subsequent calculations, the room temperature and the room pressure are measured using a thermometer and a pressure gauge.

S108: Calculating the solubility of elemental sulfur in the sulfur-containing gas based on the sampling temperature, the sampling pressure, the room temperature, the room pressure, the mass of the elemental sulfur, and the volume of the sulfur-containing gas at the room temperature and the room pressure.

Specifically, this step comprises sub-steps S1081, S1082, and S1083. The details are described below.

S1081: Calculating the volume of the sulfur-containing gas at the standard state based on the room temperature, the room pressure, and the volume of the sulfur-containing gas at the room temperature and the room pressure. The calculation equation is:

$$V_0 = \frac{P_1 \times V_1 \times (273.15 + T_0)}{P_0 \times (273.15 + T_1)};$$

in the equation, $V_0$—Volume of the sulfur-containing gas at the standard state;
$P_0$—Pressure at the standard state;
$T_0$—Temperature at the standard state;
$P_1$—Room pressure
$V_1$—Volume of the sulfur-containing gas at the room temperature and the room pressure;
$T_1$—Room temperature.

The pressure at the standard state is one atmosphere, and the temperature at the standard state is 20° C.

S1082: Calculating the volume of the sulfur-containing gas at the sampling temperature and the sampling pressure based on the volume of the sulfur-containing gas at the standard state, the sampling temperature and the sampling pressure. The calculation equation is:

$$V_1' = \frac{P_0 \times V_0 \times (273.15 + T) \times Z}{P \times (273.15 + T_0)};$$

in the equation, $V_1'$—Volume of the sulfur-containing gas at the sampling temperature and the sampling pressure;
$P_0$—Pressure at the standard state;
$V_0$—Volume of the sulfur-containing gas at the standard state;
$T_0$—Temperature at the standard state;
P—Sampling pressure;
T—Sampling temperature;
Z—Deviation factor of the gas at the sampling temperature and the sampling pressure.

Herein, the deviation factor Z of the gas at the sampling temperature and the sampling pressure can be obtained by a conventional phase experiment of the gas.

S1083: Calculating the solubility of the elemental sulfur of the sulfur-containing gas based on the volume of the sulfur-containing gas at the sampling temperature and the sampling pressure and the mass of the elemental sulfur. The calculation equation is:

$$c = \frac{m}{V_1'};$$

in the equation,
c—Solubility of elemental sulfur in the sulfur-containing gas;
m—Mass of elemental sulfur;
$V_1'$—Volume of the sulfur-containing gas at the sampling temperature and the sampling pressure.

During the experiment using the experimental device, in the process of the sulfur-containing gas flowing from the back-pressure valve to the adsorption tank, there may be a small amount of elemental sulfur remaining on the pipeline between the back-pressure valve 4 and the adsorption tank 6. In order to improve the accuracy of the experiment, after the end of the experiment, the pipeline between the sample dispenser 3 and the adsorption tank 6 can be cleaned with a carbon disulfide liquid, and the carbon disulfide liquid after washing is collected and transferred to the recovery tank 9, so that the finally measured elemental sulfur mass is more accurate.

In order to prevent the gas from polluting the environment, as shown in FIG. 1, the exhaust gas absorption tank 8 is connected to the outlet of the flow meter 7. Thus, the exhaust gas absorption tank 8 adsorbs harmful gases in the gas to prevent contamination of the environment.

As an improvement of the present disclosure, for the same gas well, the solubility $c_i$ of elemental sulfur in the corresponding sulfur-containing gas under different conditions of sampling temperatures and sampling pressure is obtained by changing the sampling temperature and the sampling pressure.

According to the Chrastil equation:

$$c = d^k \exp\left(\frac{a}{T} - b\right);$$

In the equation,
c—Solubility of solid solutes in the fluid;
d—Fluid density;
T—Temperature;
a, b k—Constants.

Taking the logarithm of two sides of the Chrastil equation, it produces:

$$\ln c = k \ln d + \frac{a}{T} + b;$$

assuming $y = \ln c$, $x_1 = \ln d$ $$x_2 = \frac{1}{T},$$

then the above equation is transformed into: $y = kx_1 + ax_2 + b$; the values of a, b, k are calculated by substituting the obtained $c_i$ value into the transformed equation. Therefore, after determining the sampling temperature and the fluid density, the solubility of elemental sulfur in the sulfur-containing gas can be determined according to the equation $y = kx_1 + ax_2 + b$ without experimentation, which is simpler.

In the examples provided in the present application, it should be understood that the terms "first", "second", and the like are used for descriptive purposes only, and are not to be construed as indicating or implying relative importance or implicitly indicating the number of technical features referred to.

The above description is only for the convenience of those skilled in the art to understand the technical solutions of the present invention, and is not intended to limit the present invention. Any modifications, equivalent substitutions, improvements, and the like made within the spirit and principle of the present invention are intended to be included within the scope of the present invention.

The invention claimed is:

1. A device for determining the solubility of elemental sulfur in a sulfur-containing gas, wherein the device comprises a displacement pump, a first sampler, a high-temperature box, a back-pressure pump, a control valve, an adsorption tank, a low-temperature box, a flow meter and a collection tank, wherein an outlet of the displacement pump is in communication with an inlet of the first sampler, an outlet of the first sampler is in communication with a first inlet of the control valve, a second inlet of the control valve is in communication with an outlet of the back-pressure pump, an outlet of the control valve is in communication with a first opening of the adsorption tank, and a second opening of the adsorption tank is in communication with the flow meter; a third opening of the adsorption tank is in communication with the collection tank;

the first sampler is located in the high-temperature box, the adsorption tank is located in the low-temperature box, a valve is arranged between the outlet of the first sampler and the first inlet of the control valve, and a valve is arranged between the third opening of the adsorption tank and the collection tank, and the collection tank is adapted for being heated.

2. The device according to claim 1, further comprising a sample dispenser, an outlet of the first sampler is in communication with an inlet of the sample dispenser, an outlet of the sample dispenser is in communication with the first inlet of the control valve, and the sample dispenser is located in the high-temperature box.

3. The device according to claim 2, wherein a filter is arranged between the outlet of the sample dispenser and the first inlet of the control valve.

4. The device according to claim 1, further comprising a second sampler, an inlet of the second sampler is in communication with the displacement pump, an outlet of the second sampler is in communication with the first inlet of the control valve.

5. The device according to claim 4, wherein a filter is arranged between the second sampler and the first inlet of the control valve.

6. The device according to claim 1, wherein a first coil is arranged between the outlet of the control valve and the first opening of the adsorption tank, and the first coil is located in the low-temperature box.

7. The device according to claim 1, wherein a second coil is arranged between the second opening of the adsorption tank and the flow meter.

8. The device according to claim 7, wherein the flow meter comprises at least two flow meters, and the at least two flow meters are connected in parallel to the downstream of the second coil, and a pneumatic valve is connected between each flow meter and the second coil.

9. The device according to claim 1, wherein an outlet of the flow meter is in communication with an exhaust gas treatment tank.

10. The device according to claim 1, further comprising a liquefaction tank, located in the low-temperature box, the collection tank is in communication with an inlet of the liquefaction tank, a check valve is arranged on a pipeline between the collection tank and the liquefaction tank to allow flow from the collection tank to the liquefaction tank.

11. The device according to claim 10 further comprising a recovery tank and a liquid injection pump, wherein the recovery tank and the liquid injection pump are each in communication with an outlet of the liquefaction tank.

12. The device according to claim 11, wherein the liquid injection pump is in communication with the third opening of the adsorption tank.

13. The device according to claim 11, further comprising a sample dispenser, an outlet of the first sampler is in communication with an inlet of the sample dispenser, an outlet of the sample dispenser is in communication with the first inlet of the control valve, and the sample dispenser is located in the high-temperature box, and wherein the liquid injection pump is connected between the sample dispenser and the first inlet of the control valve.

14. A method for determining the solubility of elemental sulfur in a sulfur-containing gas, the method comprising:
(1) collecting the sulfur-containing gas in a sulfur-containing gas reservoir, and determining a sampling temperature and a sampling pressure when the sulfur-containing gas is collected;
(2) balancing the sulfur-containing gas in step (1) to the room pressure, and then adsorbing the sulfur-containing gas with a carbon disulfide liquid;
(3) determining the volume of the sulfur-containing gas obtained after adsorption in the step (2) at the room temperature and the room pressure;
(4) heating the carbon disulfide liquid obtained after adsorbing elemental sulfur in the step (3) to remove carbon disulfide, and weighing the obtained elemental sulfur; and
(5) calculating the solubility of elemental sulfur in the sulfur-containing gas based on the sampling temperature, the sampling pressure, the room temperature, the room pressure, the mass of the elemental sulfur, and the volume of the sulfur-containing gas obtained after adsorption in the step (2) at the room temperature and the room pressure.

15. The method according to claim 14, wherein the step (5) of calculating the solubility of elemental sulfur in the sulfur-containing gas based on the sampling temperature, the sampling pressure, the room temperature, the room pressure, the mass of the elemental sulfur, and the volume of the sulfur-containing gas obtained after adsorption in the step (2) at the room temperature and the room pressure comprises:
calculating the volume of the sulfur-containing gas at the standard state based on the room temperature, the room pressure, and the volume of the sulfur-containing gas obtained after adsorption in the step (2) at the room temperature and the room pressure;
calculating the volume of the sulfur-containing gas at the sampling temperature and the sampling pressure based on the volume of the sulfur-containing gas at the standard state, the sampling temperature, and the sampling pressure;
calculating the solubility of the elemental sulfur in the sulfur-containing gas based on the volume of the sulfur-containing gas at the sampling temperature and the sampling pressure and the mass of the elemental sulfur.

16. The method according to claim 15, wherein the calculation of the volume of the sulfur-containing gas at the standard state based on the room temperature, the room pressure, and the volume of the sulfur-containing gas obtained after adsorption in the step (2) at the room temperature and the room pressure comprises calculating the volume of the sulfur-containing gas at the standard state by using the following equation (1);

$$V_0 = \frac{P_1 \times V_1 \times (273.15 + T_0)}{P_0 \times (273.15 + T_1)}; \qquad \text{Equation (1)}$$

in equation (1),
$V_0$—Volume of the sulfur-containing gas at the standard state;
$P_0$—Pressure at the standard state;
$T_0$—Temperature at the standard state;
$P_1$—Room pressure
$V_1$—Volume of the sulfur-containing gas at the room temperature and the room pressure;
$T_1$—Room temperature.

17. The method according to claim 15, wherein the calculation of the volume of the sulfur-containing gas at the sampling temperature and the sampling pressure based on the volume of the sulfur-containing gas at the standard state, the sampling temperature, and the sampling pressure comprises calculating the volume of the sulfur-containing gas at the sampling temperature and the sampling pressure by using the following equation (2);

$$V_1' = \frac{P_0 \times V_0 \times (273.15 + T) \times Z}{P \times (273.15 + T_0)}; \qquad \text{Equation (2)}$$

in equation (2),
$V_1'$—Volume of the sulfur-containing gas at the sampling temperature and the sampling pressure;
$P_0$—Pressure at the standard state;
$V_0$—Volume of the sulfur-containing gas at the standard state;
$T_0$—Temperature at the standard state;
P—Sampling pressure;
T—Sampling temperature;
Z—Deviation factor of the gas at the sampling temperature and the sampling pressure.

18. The method according to claim 15, wherein the calculation of the solubility of the elemental sulfur in the sulfur-containing gas based on the volume of the sulfur-containing gas at the sampling temperature and the sampling pressure and the mass of the elemental sulfur comprises calculating the solubility of the elemental sulfur in the sulfur-containing gas by using the following equation (3);

$$c = \frac{m}{V_1'}; \qquad \text{Equation (3)}$$

in equation (3),
c—Solubility of elemental sulfur in the sulfur-containing gas;
m—Mass of elemental sulfur;
$V_1'$—Volume of the sulfur-containing gas at the sampling temperature and the sampling pressure.

19. The method according to claim 14, wherein the method specifically comprises the following steps:
(1) collecting the sulfur-containing gas in a sulfur-containing gas reservoir, and determining a sampling temperature and a sampling pressure when the sulfur-containing gas is collected;

(2) transferring the sulfur-containing gas into a sample dispenser, and allowing the sample dispenser to swing at a preset temperature and a preset pressure for a preset duration to prevent elemental sulfur in the sulfur-containing gas from being precipitated;

(3) balancing the sulfur-containing gas in the step (2) to the room pressure, and then flowing into an adsorption tank, wherein the adsorption tank contains a carbon disulfide liquid;

(4) passing the gas flowing out of the adsorption tank through a gas flow meter, which measures the volume of the sulfur-containing gas obtained in the step (3) at the room temperature and the room pressure;

(5) collecting and transferring the carbon disulfide liquid in the adsorption tank to a collection tank; heating the collection tank to remove carbon disulfide, cooling, and determining the mass of elemental sulfur in the collection tank;

(6) calculating the solubility of elemental sulfur in the sulfur-containing gas based on the sampling temperature, the sampling pressure, the room temperature, the room pressure, the mass of the elemental sulfur, and the volume of the sulfur-containing gas obtained in the step (3) at the room temperature and the room pressure.

20. The method according to claim 19, wherein before the step (5), the method further comprises: washing a pipeline between the sample dispenser and the adsorption tank with a carbon disulfide liquid, and collecting and transferring the carbon disulfide liquid after washing into the collection tank.

* * * * *